United States Patent [19]

Kan et al.

[11] Patent Number: 4,565,814

[45] Date of Patent: Jan. 21, 1986

[54] PYRIDAZINE DERIVATIVES HAVING A PSYCHOTROPIC ACTION AND COMPOSITIONS

[75] Inventors: Jean-Paul Kan; Kathleen Biziere, both of Clapiers; Camille-Georges Wermuth, Strasbourg, all of France

[73] Assignee: Sanofi, Paris, France

[21] Appl. No.: 571,696

[22] Filed: Jan. 18, 1984

[30] Foreign Application Priority Data

Jan. 28, 1983 [FR] France ................................ 83 01366
Nov. 18, 1983 [FR] France ................................ 83 18433

[51] Int. Cl.[4] .................. A61K 31/535; C07D 413/12; C07D 413/14
[52] U.S. Cl. ..................................... 514/228; 514/229; 514/230; 514/232; 514/236; 514/237; 544/114
[58] Field of Search ................ 544/114; 514/228, 229, 514/230, 232, 236, 237

[56] References Cited

PUBLICATIONS

European Patent Application 74,863, 3-23-83.

Primary Examiner—Robert W. Ramsuer
Attorney, Agent, or Firm—Bacon & Thomas

[57] ABSTRACT

This invention relates to pyridazine derivatives substituted in the 4-position by a cyano group having psychotropic activity. It also relates to a process for the preparation of these products and their application as medicaments.

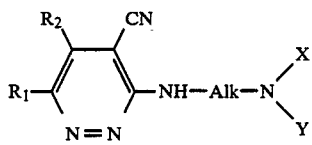

13 Claims, No Drawings

PYRIDAZINE DERIVATIVES HAVING A PSYCHOTROPIC ACTION AND COMPOSITIONS

Pyridazine derivatives have been proposed as medicaments for many years. In a large number of cases, these are substances which are active on the cardiovascular system and which have, in particular, a hypotensive or vasodilatory effect. More rarely, pyridazine derivatives have been mentioned as having an antiinflammatory and analgesic action. Finally, French Pat. No. 2,141,697 describes a family of products corresponding to the general formula:

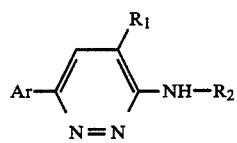

in which:
$R_1$ represents hydrogen or a lower alkyl group;
Ar represents an aromatic radical; and
$R_2$ denotes a group:

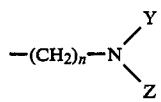

in which n=2 or 3 and Y and Z represent a lower alkyl group, or alternatively

constitutes a heterocyclic radical.

These compounds are characterised by a psychotropic activity of the psychotonic type.

It has now been found that the introduction of the cyano group into the 4-position of pyridazine substantially improves the therapeutic properties of these products compared with the properties described for the same family of pyridazines unsubstituted in the 4-position or substituted in the same position by a methyl group, the best-known example of which is minaprine (DCI) (Ar=$C_6H_5$, $R_1$=$CH_3$, $R_2$=$\beta$-morpholinoethyl).

Thus, according to one of its features, the present invention relates to 4-cyanopyridazines having the following formula:

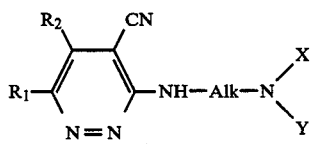

in which:
one of the substituents $R_1$ and $R_2$ represents hydrogen or a lower alkyl group and the other represents hydrogen; a $C_1$-$C_6$ alkyl group; a $C_3$-$C_7$ cycloalkyl group; a phenyl group; a phenyl group monosubstituted by a halogen atom, a nitro group, a trifluoromethyl group, a hydroxyl group, a $C_1$-$C_6$ alkoxy group, a $C_1$-$C_6$ alkyl group, a $C_1$-$C_6$ alkanoyloxy group, a cyano group, a $C_1$-$C_6$ alkylthio group, a $C_1$-$C_6$ alkylsulphinyl group, a $C_1$-$C_6$ alkylsulphonyl group or a sulphamyl group; a phenyl group disubstituted by one of the abovementioned substituents on the one hand and a chlorine or fluorine atom or a methoxy group on the other; a naphth-1-yl group; a naphth-2-yl group; a thien-2-yl group; a thien-3-yl group; or an indol-3-yl group;
Alk represents an ethylene group, a 1,2-propylene group or a 1,3-propylene group;
X denotes hydrogen; and
Y represents hydrogen or a $\beta$-hydroxyethyl group, or alteratively The group

represents a morpholin-4-yl or 3-oxomorpholin-4-yl group,
and also their pharmaceutically acceptable salts.

Comparison of the products of the invention with minaprine in several pharmacological tests, demonstrating their psychotropic activity, showed that the products according to the invention have a median effective dose which is comparable to or less than that of minaprine, while their toxicity is considerably lower. Thus, the compounds according to the invention have a very much higher therapeutic index than minaprine.

According to another feature, the present invention relates to a process for the preparation of the compounds of the formula I in which $R_1$, $R_2$, Alk, X and Y are as defined above, which is represented by the following scheme:

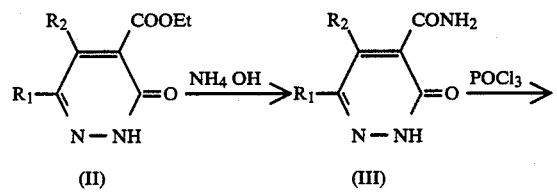

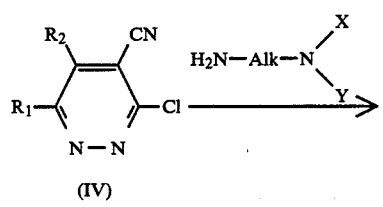

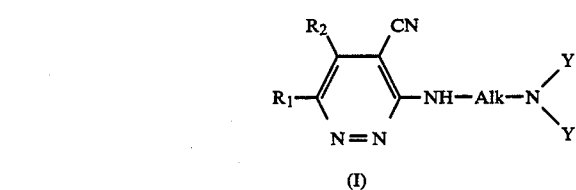

The process of the present invention is characterised in that the following reactions are carried out:
(a) an appropriately substituted 4-ethoxycarbonylpyridazone (II) is treated with aqueous ammonia to give the corresponding pyridazone-4-carboxamide (III);

(b) the pyridazone-4-carboxamide is treated with phosphorus oxychloride to give the 3-chloro-4-cyanopyridazine (IV); and (c) by reaction with the amine $$H_2N-Alk-N\begin{matrix}X\\ \\Y\end{matrix},$$

the pyridazine is substituted in the 3-position to give the compound (I).

In the first step, excess concentrated aqueous ammonia solution is used and the reaction is carried out at ambient temperature for 10 to 15 hours.

The second step is carried out with excess phosphorus oxychloride at a temperature of about 80° C. for several hours.

Finally, the last step is carried out by heating the two reactants in a suitable solvent such as n-butanol.

Most of the starting materials are known. Those which are not can easily be prepared, for example by reacting an α-halogenoketone of the formula:

$$R_1-\underset{\underset{O}{\|}}{C}-\underset{\underset{R_2}{|}}{CH}-Hal \qquad (A)$$

in which Hal is a chlorine or bromine atom, with ethyl malonate to form the substituted malonate:

$$R_1-\underset{\underset{O}{\|}}{C}-\underset{\underset{R_2}{|}}{CH}-CH\begin{matrix}COOC_2H_5\\ \\COOC_2H_5\end{matrix} \qquad (B)$$

This is treated with hydrazine to give the product of the formula:

[structure with $R_1$, $R_2$, COOC$_2$H$_5$, =O, N—N, H]

which, on dehydrogenation, for example with bromine in acetic acid, yields the desired product II.

The key intermediates in the process of the present invention, which have the formulae III and IV above, are new products if at least one of the substituents $R_1$ and $R_2$ is other than hydrogen or the methyl group.

According to another feature, the present invention also relates to these compounds of the formulae III and IV as new products which can be used as intermediates.

Finally, according to yet another feature, the present invention relates to pharmaceutical compositions containing, as active products, the compounds of the formula I above or their pharmaceutically acceptable salts.

In the pharmaceutical compositions of the present invention for oral, sublingual, subcutaneous, intramuscular, intravenous, transdermal or rectal administration, the active ingredients of the formula I above can be administered to mammals, including humans, in unit forms of administration, as a mixture with conventional pharmaceutical carriers, for the treatment of various neurological and psychiatric complaints: mood and behaviour disorders, neurological and endogenous depressions, memory disorders, infantile hyperkinesis, antism, and sexual insufficiencies of psychogenic origin.

Suitable unit forms of administration which must be mentioned include forms for oral administration, such as tablets, gelatine capsules, powders, granules and solutions or suspensions to be taken orally, and forms of sublingual and buccal administration, and also forms of parenteral administration which can be used for subcutaneous, intramuscular or intravenous administration.

To obtain the desired therapeutic effect, the dose of active principle can vary between 0.1 and 50 mg per kg of body weight per day.

Each unit dose can contain from 1 to 500 mg of active ingredient in combination with a suitable pharmaceutical carrier. It can be administered from 1 to 4 times per day.

The examples which follow illustrate the invention without however limiting it.

PREPARATION 1

(a) Ethyl phenacylmalonate 240.25 g of ethyl malonate, 138 g of potassium carbonate, 5 g of potassium iodide and 154 g of phenacyl chloride in 2 liters of anhydrous acetone are heated under reflux overnight.

After the inorganic salts have been filtered off, the filtrate is evaporated to dryness and the excess ethyl malonate is then distilled off under reduced pressure (pressure: 0.5 mbar; temperature: about 60° C.). The distillation residue is chromatographed on a silica column using a cyclohexane/ethyl acetate mixture (9/1) as the eluent. The expected ketoester is in the form of a red oil. Yield: 80.3%.

(b) 4-Ethoxycarbonyl-6-phenyl-4,5-dihydro-2H-pyridazin-3-one 40.5 g of the previously obtained product are dissolved in 70 ml of absolute ethanol, and 7.25 g of hydrazine hydrate are added dropwise to the reaction medium at a temperature of the order of 0° C., with stirring. When the reaction medium has returned to ambient temperature, it is stirred for 24 hours and the beige precipitate obtained, which corresponds to the expected pyridazinone, is then filtered off.

The filtrate is treated with 3.62 g of hydrazine hydrate. After stirring for 24 hours, an additional quantity of pyridazinone can be filtered off. The same operation is repeated once more on the filtrate.

After purification by passage through a silica column using a cyclohexane/ethyl acetate mixture (volume volume: 1/1) as the eluent, the expected compound is obtained with a yield of 37%.

(c) 4-Ethoxycarbonyl-6-phenyl-2H-pyridazin-3-one (II) $R_1=C_6H_5$; $R_2=H$ 9 g of the compound obtained under (b) are dissolved in 200 ml of acetic acid, and 11.18 g of bromine are then added to the solution, with stirring. Decolouration of the medium occurs after 5 minutes. After 2 hours at ambient temperature, and with stirring, the medium is poured into 200 ml of water, the mixture is then extracted with methylene chloride and the organic phase is evaporated to dryness.

The residue is taken up three times with cyclohexane. The beige powder obtained is chromatographed on a silica column using a cyclohexane/ethyl acetate mixture (volume/volume: 1/1) as the eluent. The expected pyridazinone is obtained with a yield of 51%. Melting point 150° C.

PREPARATION 2 to 8

The products (II) described in Table 1 are obtained, following the procedure described in Preparation 1, starting from:
para-chlorophenyl chloromethyl ketone,
para-fluorophenyl chloromethyl ketone,
α-naphthyl bromomethyl ketone,
cyclohexyl chloromethyl ketone,
2,4-dichlorophenyl chloromethyl ketone,
indol-3-yl chloromethyl ketone,
thien-3-yl chloromethyl ketone,
by reaction with ethyl malonate, condensation with hydrazine hydrate and dehydrogenation with bromine in acetic acid.

TABLE 1

| Preparation No. | R1 | R2 |
|---|---|---|
| 2 |  | H |
| 3 |  | H |
| 4 |  | H |
| 5 |  | H |
| 6 |  | H |
| 7 | 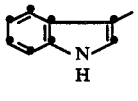 | H |
| 8 |  | H |

PREPARATIONS 9 TO 18

The products described in Table 2 are obtained, following the procedure described in Preparation 1, starting from:
4-methoxyphenyl chloromethyl ketone,
4-hydroxyphenyl chloromethyl ketone,
3,4-dimethoxyphenyl chloromethyl ketone,
4-nitrophenyl chloromethyl ketone,
3-methylphenyl chloromethyl ketone,
cyclopentyl chloromethyl ketone,
3-trifluoromethylphenyl chloromethyl ketone,
phenyl 1-chloroethyl ketone,
methyl α-chlorobenzyl ketone,
α-chlorophenylacetaldehyde,
by reaction with ethyl malonate, condensation with hydrazine hydrate and dehydrogenation with bromine in acetic acid.

TABLE 2

| Preparation No. | R1 | R2 |
|---|---|---|
| 9 | 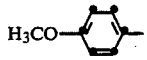 | H |
| 10 | 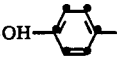 | H |
| 11 | 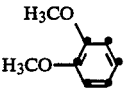 | H |
| 12 |  | H |
| 13 | 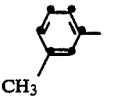 | H |
| 14 |  | H |
| 15 | 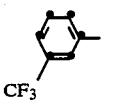 | H |
| 16 |  | CH3 |
| 17 | CH3 |  |
| 18 | H |  |

PREPARATIONS 19 TO 36

The products mentioned in Table 3 are obtained in the same way, starting from:
4-methylthiophenyl chloromethyl ketone,
4-methylsulphinylphenyl chloromethyl ketone,
4-methylsulphonylphenyl chloromethyl ketone,
naphth-2-yl chloromethyl ketone,
thien-2-yl chloromethyl ketone,
2-chlorophenyl chloromethyl ketone,
3-chlorophenyl chloromethyl ketone,
3,4-dichlorophenyl chloromethyl ketone,
cyclopropyl chloromethyl ketone,
4-methylphenyl chloromethyl ketone,
2-methylphenyl chloromethyl ketone,
4-trifluoromethylphenyl chloromethyl ketone,
cyclooctyl chloromethyl ketone,
4-cyanophenyl chloromethyl ketone,
4-sulphamoylphenyl chloromethyl ketone,
3,4-dihydroxyphenyl chloromethyl ketone,
4-acetoxyphenyl chloromethyl ketone,
α-bromodeoxybenzoin.

TABLE 3

| Preparation No | Compounds II R1 | R2 |
|---|---|---|
| 19 | CH₃S—⌬— | H |
| 20 | CH₃SO—⌬— | H |
| 21 | CH₃SO₂—⌬— | H |
| 22 | naphthyl | H |
| 23 | thienyl (2-) | H |
| 24 | 3-Cl-phenyl | H |
| 25 | 4-Cl-phenyl | H |
| 26 | 3,4-diCl-phenyl | H |
| 27 | cyclopropyl | H |
| 28 | H₃C—⌬— | H |
| 29 | 2-CH₃-phenyl | H |
| 30 | F₃C—⌬— | H |
| 31 | cyclooctyl | H |
| 32 | NC—⌬— | H |
| 33 | H₂NSO₂—⌬— | H |
| 34 | 3,4-diHO-phenyl | H |
| 35 | CH₃COO—⌬— | H |
| 36 | phenyl | phenyl |

EXAMPLE 1

6-Phenyl-3-oxo-2H-pyridazine-4-carboxamide (III) R₁=C₆H₅; R₂=H 2 g of the product obtained in Preparation 1 are added to 40 ml of concentrated ammonia solution and the mixture is stirred overnight at ambient temperature. The solid is filtered off and dried to give the expected product.

Yield 86%; melting point > 300° C.

EXAMPLES 2 TO 17

The compounds III described in Table 4 are obtained, following the procedure of Example 1, starting from the corresponding ethoxycarbonyl derivatives.

TABLE 4

| Example No | Compounds III R1 | R2 |
|---|---|---|
| 2 | Cl—⌬— | H |
| 3 | F—⌬— | H |
| 4 | naphthyl | H |
| 5 | pyridyl | H |
| 6 | 3,4-diCl-phenyl | H |
| 7 | 2-Cl-phenyl | H |
| 8 | thienyl | H |
| 9 | H₃CO—⌬— | H |
| 10 | 3,4-diCl-phenyl | H |
| 11 | naphthyl | H |

TABLE 4-continued

| Example No | Compounds III R1 | R2 |
|---|---|---|
| 12 | 4-O₂N-C₆H₄- | H |
| 13 | 4-H₃C-C₆H₄- | H |
| 14 | 4-F₃C-C₆H₄- | H |
| 15 | 3-CF₃-C₆H₄- | H |
| 16 | C₆H₅- | C₆H₅- |
| 17 | 4-NC-C₆H₄- | H |

EXAMPLE 18

3-Chloro-4-cyano-6-phenylpyridazine (IV) R₁=C₆H₅; R₂=H 1.5 g of the product obtained in Example 1 are dissolved in 20 ml of phosphorus oxychloride and the solution is then heated at 80° C. for 5 hours. The mixture is poured into 50 ml of water. A precipitate appears, which is filtered off and dried.

Yield: 58.3%; melting point 206° C.

EXAMPLES 19 TO 34

The 3-chloro-4-cyanopyridazines of the formula IV described in Table 5 are obtained, following the procedure of Example 18, starting from the corresponding amides of the formula III.

TABLE 5

| Example No. | Compounds IV R₁ | R₂ | Melting point or Rf |
|---|---|---|---|
| 19 | 4-Cl-C₆H₄- | H | Chromatography |
| 20 | 4-F-C₆H₄- | H | Melting point: 170° C. |
| 21 | naphthyl | H | Chromatography |
| 22 | cyclohexyl | H | Rf: 0.9 (hexane - ethyl acetate) |
| 23 | 3,4-Cl₂-C₆H₃- | H | Melting point: 152–154° C. |
| 24 | 2-Cl-C₆H₄- | H | Rf: 0.4 (hexane - ethyl acetate 2/1) |
| 25 | 2-thienyl | H | Melting point: 152° C. |
| 26 | 4-H₃CO-C₆H₄- | H | Melting point 196–198° C. |
| 27 | 2,6-Cl₂-C₆H₃- | H | Melting point 204–206° C. |
| 28 | 6-methyl-2-naphthyl | H | Melting point: 231–232° C. |
| 29 | 4-O₂N-C₆H₄- | H | Rf: 0.8 (hexane - ethyl acetate 2/1) |
| 30 | 4-H₃C-C₆H₄- | H | Melting point 191° C. |
| 31 | 4-F₃C-C₆H₄- | H | Rf: 0.7 (hexane - ethyl acetate 2/1) |
| 32 | 3-CF₃-C₆H₄- | H | Rf: 0.8 (hexane - ethyl acetate 1/1) |
| 33 | C₆H₅- | C₆H₅- | — |
| 34 | 4-NC-C₆H₄- | H | Rf: 0.9 (hexane - ethyl acetate 1/1, vol/vol) |

EXAMPLE 35

3-(2-Morpholinoethylamino)-4-cyano-6-phenylpyridazine dihydrochloride. SR 95 191.

(I) R₁=C₆H₅; R₂=H; Alk=(CH₂)₂;

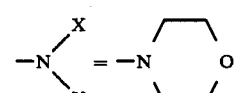

7.3 g of the chlorine compound of Example 18 are dissolved in 60 ml of normal butanol, and 8 g of N-(2-aminoethyl)-morpholine are added. The mixture is heated under reflux for 3 hours and then poured into 1000 ml of water. The organic phase is extracted with ether and the ether solution is then extracted with a 1N solution of sulphuric acid. The aqueous phase is separated off, rendered alkaline with sodium hydroxide and extracted with ether. The ether phase is dried over magnesium sulphate and the solvent is then evaporated off to dryness in vacuo. This gives a yellow solid. Yield 81.3%; melting point 138° C.

6.8 g of the product obtained above are dissolved in 100 ml of dry methanol, and a stream of hydrogen chloride is bubbled into the solution. The solvent is evaporated off to dryness in vacuo and the residue is taken up with anhydrous ether.

A precipitate of 3-(2-morpholinoethylamino)-4-cyano-6-phenylpyridazine dihydrochloride forms, which is recrystallised twice from isopropanol. Melting point 144° C. (decomposition).

Starting from the base, the following salts of the same compound can be prepared in the same manner:

| | |
|---|---|
| Monocitrate | Melting point 181° C. (aqueous ethanol) |
| Diglutamate | Melting point above 260° C. (aqueous ethanol) |
| Monohydrochloride | Melting point 230° C. |
| Monofumarate | Melting point 204° C. (acetone) |
| Monomaleate | Melting point 168° C. (acetone) |

EXAMPLES 36 TO 51

The compounds (I) described in Table 6 are obtained, following the procedure described above, by reacting the corresponding chlorinated derivative of the formula (IV) with N-(2-aminoethyl)-morpholine.

TABLE 6

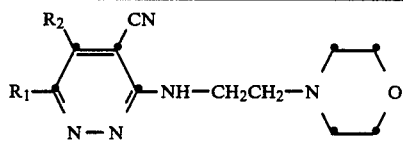

| Example | SR Product Code No. | $R_1$ | $R_2$ | Salt or base Melting point (°C.) (solvent) |
|---|---|---|---|---|
| 36 | 95276 A | Cl-phenyl | H | Dihydrochloride 135–140 (decomposition) |
| 37 | 95306 | F-phenyl | H | Base 208 |
| 38 | 95294 A | naphthyl | H | Dihydrochloride 130–140 (decomposition isopropanol) |
| 39 | 95331 A | cyclohexyl | H | Dihydrochloride 168 (decomposition) |
| 40 | 42632 A | 2,4-Cl,Cl-phenyl | H | Fumarate (2/3) 183–185 (acetone) with 0.5 H₂O |
| 41 | 95324 A | 2-Cl-phenyl | H | Dihydrochloride 228 (isopropanol) |
| 42 | 95274 A | thienyl | H | Dihydrochloride 170 (methanol) |
| 43 | 42595 A | H₃CO-phenyl | H | Fumarate (1/1) 240–242 (acetone) |
| 44 | 42638 A | 3,4-Cl,Cl-phenyl | H | Maleate (1/1) 240–242 (acetone) |
| 45 | 42692 | naphthyl | H | Base 184–186 (isopropanol) |
| 46 | 95323 A | O₂N-phenyl | H | Dihydrochloride 260 (decomposition) |
| 47 | 42639 | H₃C-phenyl | H | Base 150–151 (isopropanol) |
| 48 | 95330 A | F₃C-phenyl | H | Dihydrochloride 278 Base 159 |
| 49 | 95328 | 3-CF₃-phenyl | H | Base 129 |
| 50 | 95071 A | phenyl-phenyl | | Monohydrochloride 210 (decomposition) |
| 51 | 95329 | NC-phenyl | H | Base 205 (methanol) |

EXAMPLES 52 TO 56

The compounds (I) collated in Table 7 are obtained from various 3-chloropyridazines following the procedure of Example 35, but varying the amine compound used.

TABLE 7

$$-N\begin{matrix} X \\ Y \end{matrix}$$

| Example No | SR Code No. | R₁ | R₂ | Alk | $-N<^X_Y$ | Base or salt Melting point °C. |
|---|---|---|---|---|---|---|
| 52 | 95290 A | phenyl | H | (CH₂)₂ | —NH₂ | Dihydrochloride 130–140 |
| 53 | 95291 A | " | H | " | —NH—CH₂CH₂OH | Dihydrochloride 110–110 (hygroscopic) |
| 54 | 95332 A | thienyl (2-thienyl) | H | " | " | Dihydrochloride 124 (decomposition) |
| 55 | 95292 A | phenyl | H | CH₂—CH— \| CH₃ | morpholino (—N⟨⟩O) | Dihydrochloride 135–140 (decomposition) |
| 56 | 42633 | 4-F-phenyl 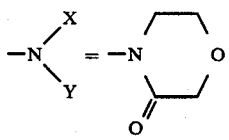 | H | (CH₂)₂ | —NH₂ | Base 200–202 (ethanol) |

EXAMPLE 57

3-[2-(3-Oxomorpholino)-ethylamino]-4-cyano-6-phenylpyridazine hydrochloride. SR 95327 A $R_1=C_6H_5$; $R_2=H$; $Alk=(CH_2)_2$;

$$-N\begin{matrix}X\\Y\end{matrix} = -N\underset{O}{\overset{\diagup\phantom{O}\diagdown}{\diagdown\phantom{O}\diagup}}O$$

(a) A solution of 4.2 g of sodium hydroxide in 54 ml of water is added to a solution of 3 g of compound 95291 A (Example 53) in 54 ml of methylene chloride and the mixture is then cooled to $-5°$ C., $-10°$ C., with stirring. 1.17 g of chloroacetyl chloride are added slowly, the temperature is then allowed to rise to 20° C. and the mixture is left for 15 hours at this temperature, with stirring. The organic phase is separated off and evaporated to dryness in vacuo.

This gives a yellow solid, which is used as such for the following step:

(b) The product obtained above is dissolved in 27 ml of anhydrous methanol, and a solution of sodium methylate, obtained by reacting 0.24 g of sodium with 27 ml of anhydrous methanol, is added. The mixture is heated under reflux for 6 hours and evaporated to dryness. The residue is taken up in water and extracted with ethyl acetate. The organic layer is separated off, dried over sodium sulphate and evaporated to dryness. The product is purified by chromatography on a silica column using an ethyl acetate/methanol mixture, 8/2 vol/vol, as the This gives a pale yellow oil (1.5 g). This is dissolved in methanol and dry hydrogen chloride is bubbled into the solution. The mixture is evaporated to dryness and the residue is taken up in the minimum quantity of methanol. Anhydrous ether is added and the precipitate of hydrochloride is filtered off; melting point 128° C.

EXAMPLE 58

Galenical preparation

The gelatine capsules containing the following ingredients may be indicated as an example of a galenical preparation:

| | |
|---|---|
| Active principle | 50 mg |
| Aerosil | 0.5 mg |
| Magnesium stearate | 1.5 mg |
| STA RX 1500 starch | 48 mg |
| | 100 mg |

The psychotropic activity of a compound representative of the invention, namely compound SR 95191 (Example 37), was measured in three pharmacological tests and compared with minaprine and iminaprine, which is a very widely used antidepressant. Likewise, the toxicity of the product was compared with that of the reference products.

DESPAIR BEHAVIOUR

This test was carried out on CD1 (Charles River) female mice, weighing 18 to 23 g, by the method described by PORSOLT (*Archives Internationales de Pharmacodynamie,* 1977, 327–336).

The principle of this test is as follows: when a mouse is placed in a narrow vessel filled with water, it struggles and then, after 2 to 4 minutes, it becomes immobile and floats on its abdomen, with its back hunched and its back paws tucked under the body, and it only makes the few movements necessary to keep its head above the water. This is the so-called despair reaction.

Certain psychotropic drugs, in particular antidepressants, lengthen the time for which the mouse struggles.

The following protocol was selected:

The products to be studied were administered intraperitoneally 1 hour before the test. For the test, the animals are placed in a narrow vessel (10×10×10 cm) filled with water to a height of 6 cm, the temperature being 24° C. plus or minus 2° C. The animals are left in the water for 6 minutes and the time for which the animal remains immobile between the 2nd and 6th minutes is measured. The activity of the substance is the greater, the shorter this time.

Each substance was studied on a batch of 10 mice. The results are the average of at least two experiments.

ANTAGONISM OF RESERPINE-INDUCED PTOSIS

This test, which is described by GOURET (*Journal de pharmacologie Paris* 1973, 4 (1), 105–128), was carried out on CD1 (Charles River) female mice weighing 20 g plus or minus 1 g. Reserpine causes ptosis 1 hour after its intravenous administration; certain antidepressants oppose this ptosis.

The following protocol was selected:

The substances to be studied were administered intraperitoneally. The reserpine is administered intravenously at the same time, at a dose of 2 mg/kg. 1 hour after the administration of reserpine, the number of animals which do not exhibit ptosis are noted.

This test was carried out on batches of 10 mice; the results are expressed as a percentage of animals which do not exhibit ptosis and are the average of at least two experiments.

ROTATIONAL BEHAVIOUR

This test is described by PROTAIS et al. in *Journal de pharmacologie*, 1976, 7, 251–255.

CD1 Charles River female mice weighing from 20 to 24 g first undergo unilateral lesion of the striatum by the stereotaxic injection of 6-hydroxydopamine at a dose of 8 µg per animal. One week after this operation, the product is administered intraperitoneally to groups of 7 mice. The number of rotations is evaluated over 2 minutes, 1 hour after the administration of the product. Rotations on the same side as the lesion are counted as positive and those on the opposite side are counted as negative. The algebraic sum of the rotations for a group of treated animals is compared with that for the group of control animals, which have only received the vehicle (physiological serum).

ACUTE TOXICITY

The products to be studied were administered intraperitoneally in increasing doses to batches of 10 mice. The mortality caused by the products studied was noted for 24 hours following the administration of the product.

The 50% lethal dose, that is to say the dose causing the depth of 50% of the animals studied, is determined from the results obtained for each of the products studied.

The results obtained are shown in Table 8.

TABLE 8

| Compound | Toxicity, intraperitoneal administration $LD^{50}$ | Reserpine-induced ptosis, intraperitoneal administration $ED^{50}$ | Despair behaviour, intraperitoneal administration | Rotational behaviour, intraperitoneal administration |
|---|---|---|---|---|
| SR 95191 | 250 mg/kg | 3.9 mg/kg | 5 mg/kg: −26%++ | 0.1 mg/kg: −60%++ |
|  |  |  |  | 2 mg/kg: −107%++ |
|  | 63 mg/kg | 5 mg/kg | 5 mg/kg: −31%++ | 0.125 mg/kg: −53%++ |
|  |  |  |  | 2 mg/kg: −82%++ |
|  | 89 mg/kg | 2.4 mg/kg | 10 mg/kg: −38%++ | 3 mg/kg: −6% n.s. |

++: p 0.1 Student test
n.s.: not significant

In the same manner, the psychotropic activity of two other compounds representative of the invention, namely compounds SR 95274 A (Example 42) and SR 95294 A (Example 38), was determined in two of the above pharmacological tests: rotational behaviour and antagonism of reserpine-induced ptosis. The results obtained are indicated in Table 9 below, together with the toxicity of these products administered intraperitoneally under the conditions indicated above.

TABLE 9

| Products | Toxicity, intraperitoneal administration | Test for the antagonism of reserpine-induced ptosis, intraperitoneal administration | Rotational behaviour of mice (intraperitoneal administration) |
|---|---|---|---|
| SR 95 274 A | $LD_{50}$ >300 mg/kg | $ED_{50}$ = 2.6 mg/kg | 0.5 mg/kg - 60%* 2 mg/kg - 82%* |
| SR 95 294 A |  | $ED_{50}$ = 10 mg/kg | 0.5 mg/kg - 74%* 2 mg/kg - 92%* |
| Minaprine | $LD_{50}$ = 63 mg/kg | $ED_{50}$ = 5 mg/kg | 2 mg/kg - 82%* |

*p < 0.01, Student test

We claim:

1. A 4-cyanopyridazine corresponding to the formula:

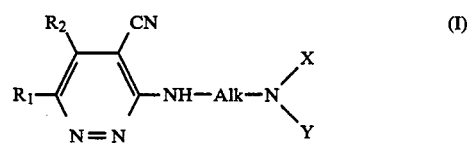

in which:
one of the substituents $R_1$ and $R_2$ represents hydrogen or a lower alkyl group and the other represents hydrogen; a $C_1$-$C_6$ alkyl group; a $C_3$-$C_7$ cycloalkyl group; a phenyl group; a phenyl group monosubstituted by a halogen atom, a trifluoromethyl group, a hydroxyl group, a $C_1$-$C_6$ alkoxy group, a $C_1$-$C_6$ alkyl group, a $C_1$-$C_6$ alkanoyloxy group, a cyano group, a $C_1$-$C_6$ alkylthio group, a $C_1$-$C_6$ alkylsulphinyl group, a $C_1$-$C_6$ alkylsulphonyl group, a nitro group, or a sulphamyl group; a phenyl group disubstituted by one of the abovementioned substituents and at least a chlorine atom, a fluorine atom or a methoxy group; a naphth-1-yl group; a naphth-2-yl group; a thien-2-yl group; a thien-3-yl group; or an indol-3-yl group;

Alk represents an ethylene group, a 1,2-propylene group or a 1,3-propylene group;
the group

represents a morpholin-4-yl or 3-oxomorpholin-4-yl group, and pharmaceutically acceptable salts thereof.

2. A compound as claimed in claim 1, wherein NXY is morpholino, Alk is —CH$_2$—CH$_2$—, R$_2$ is hydrogen and R$_1$ is selected from the group consisting of cyclohexyl, phenyl, chloropheny, fluorophenyl, dichlorophenyl, methoxyphenyl, nitrophenyl, methylphenyl, trifluoromethylphenyl, cyanophenyl, naphtyl, thien-2-yl, thien-3-yl.

3. A compound as claimed in claim 2, wherein R$_1$ is C$_6$H$_5$, R$_2$ is H and Alk is —(CH$_2$)$_2$—.

4. A compound as claimed in claim 2, wherein R$_1$ is

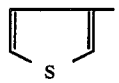

R$_2$ is H and Alk is —(CH$_2$)$_2$—.

5. A compound as claimed in claim 2, wherein R$_1$ is

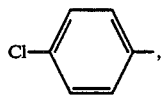

R$_2$ is H, and Alk is —(CH$_2$)$_2$—.

6. A compound as claimed in claim 2, wherein R$_1$ is

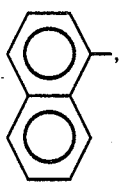

R$_2$ is H and Alk is —(CH$_2$)$_2$—.

7. A compound as claimed in claim 2, wherein R$_1$ is

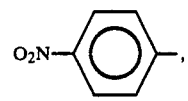

R$_2$ is H, and Alk is —(CH$_2$)$_2$—.

8. A compound as claimed in claim 2, wherein R$_1$ is

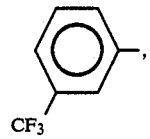

R$_2$ is H and Alk is —(CH$_2$)$_2$—.

9. A compound as claimed in claim 2, wherein R$_1$ is

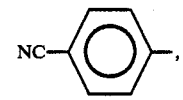

R$_2$ is H, and Alk is —(CH$_2$)$_2$—.

10. A compound as claimed in claim 2, wherein R$_1$ is

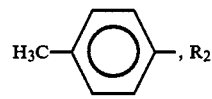

is H, and Alk is —(CH$_2$)$_2$—.

11. A compound as claimed in claim 1, wherein the group

represents 3-orymorpholin-4-yl, R$_1$ is C$_6$H$_5$, R$_2$ is H and Alk is —(CH$_2$)$_2$—.

12. A pharmaceutical composition containing as active ingredient the compound of claim 1 present in an amount sufficient to produce psychotropic action and a pharmaceutically acceptable carrier.

13. The composition of claim 12 packaged in the form of unit dosages for oral administration, said unit dosage containing 1–500 mg. of active ingredient.

* * * * *